(12) United States Patent
Amador et al.

(10) Patent No.: US 9,007,212 B2
(45) Date of Patent: Apr. 14, 2015

(54) USING A RFID PAGING INFRASTRUCTURE

(75) Inventors: Erick S. Amador, Miramar, FL (US);
Rick A. Hamilton, II, Charlottesville, VA (US); Philip K. Mullins, Richmond, TX (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 1894 days.

(21) Appl. No.: 11/550,465

(22) Filed: Oct. 18, 2006

(65) Prior Publication Data
US 2008/0094215 A1    Apr. 24, 2008

(51) Int. Cl.
| G08B 13/14 | (2006.01) |
| G08B 5/22 | (2006.01) |
| H04Q 1/30 | (2006.01) |
| G08B 21/00 | (2006.01) |
| G08B 3/10 | (2006.01) |

(52) U.S. Cl.
CPC ................................. G08B 3/1083 (2013.01)

(58) Field of Classification Search
USPC ........................................................ 340/10.1
See application file for complete search history.

(56) References Cited

U.S. PATENT DOCUMENTS

| 5,594,786 | A  * | 1/1997 | Chaco et al. ............... 379/93.09 |
| 6,566,997 | B1 * | 5/2003 | Bradin ......................... 340/10.2 |
| 7,203,727 | B2 * | 4/2007 | Suzuki et al. ................. 709/206 |
| 7,571,211 | B1 * | 8/2009 | Melick et al. ................. 709/206 |
| 2002/0075151 | A1 | 6/2002 | Lancos et al. |
| 2003/0052788 | A1 | 3/2003 | Kwong-Tai Chung |
| 2005/0197062 | A1 | 9/2005 | Sprogis |
| 2006/0055552 | A1 * | 3/2006 | Chung et al. ............... 340/686.1 |
| 2006/0111053 | A1 | 5/2006 | Wu et al. |
| 2006/0188116 | A1 * | 8/2006 | Frerking et al. ............. 381/315 |
| 2007/0259677 | A1 * | 11/2007 | Waxman ...................... 455/466 |
| 2008/0025307 | A1 * | 1/2008 | Preiss et al. .................. 370/392 |

* cited by examiner

*Primary Examiner* — Jennifer Mehmood
*Assistant Examiner* — John Mortell
(74) *Attorney, Agent, or Firm* — Yee & Associates, P.C.; Lisa J. Ulrich (57) ABSTRACT

The "RFID Paging Infrastructure" uses RFID technology to provide a low-cost localized message paging system. When a stationary RFID transceiver detects a programmable RFID tag, the transceiver reads an identifier from the RFID tag. The RFID transceiver causes a computer to determine whether a message stored in a database is intended for the RFID tag, and responsive to a determination that a message is intended for the RFID tag, the RFID transceiver transmits the message to the RFID tag. The message is saved in a memory on the programmable RFID tag. The message in the memory on the RFID tag can be read with a hand-held display device or the RFID tag can be coupled with an integrated display device.

24 Claims, 5 Drawing Sheets

USING A RFID PAGING INFRASTRUCTURE

FIELD OF THE INVENTION

The present invention relates generally to telecommunications and relates specifically to identifying a RFID tag and transmitting a message intended for the RFID tag to the RFID tag and displaying the message with a RFID tag reader.

BACKGROUND OF THE INVENTION

Message paging is an essential communication tool for the healthcare industry, particularly large medical facilities such as hospitals with multiple wings, buildings, and separate campuses. Message paging enables hospital staff to notify doctors and other personnel of emergencies, patient status, room availability, equipment failures, and other issues that may arise.

Another technology used by the healthcare industry is Radio Frequency Identification (RFID) for inventory and asset tracking. RFID tags are small electronic devices with an antenna that responds to queries from RFID transceivers. Every RFID tag has a unique identifier, and can contain other data related to the tag or to the item on which the tag is affixed. RFID tags are applied to assets and equipment such as beds, gurneys, carts, medical monitors, and computers for asset tracking. RFID tags are used with patient wrist bands for verifying identity and staff identification cards for granting access to restricted areas of the medical facility. Stationary RFID tag readers and transceivers can identify RFID tags in the vicinity of the stationary RFID tag reader, assisting hospital personnel in locating assets or people or for granting access to a restricted area. Portable RFID tag readers are used for taking inventory, or verifying a patient's identity before performing a procedure or administering medicines. Active, programmable RFID tags have a memory that can be repeatedly reprogrammed with new information. Programmable RFID tags are used, for example, with patient identification wrist bands to store and update medical information and prescribed medicine dosages.

Maintaining comprehensive cellular phone and pager coverage across a healthcare facility is essential. But the costs to support coverage by multiple telecommunication systems can be prohibitive. Programmable RFID tags are already in use, but are not presently available for message paging. Thus, a need exists for a message paging system using pre-existing RFID infrastructure.

SUMMARY OF THE INVENTION

The "RFID Paging Infrastructure" uses RFID technology to provide a low-cost localized message paging system. When a stationary RFID transceiver detects a programmable RFID tag, the transceiver reads an identifier from the RFID tag. The RFID transceiver causes a computer to determine whether a message is intended for the RFID tag, and responsive to a determination that a message is intended for the RFID tag, the RFID transceiver transmits the message to the RFID tag. The message is saved in a memory on the programmable RFID tag. The message in the memory on the RFID tag can be read with a display device.

A message can be entered into a database on a general purpose computer that stores the message with the RFID tag identifier associated with the intended recipient RFID tag. If a RFID tag is associated with a piece of equipment, a corresponding message could relate to the piece of equipment's assigned location, the equipment's status and maintenance schedule. If the RFID tag is associated with a staff member, corresponding messages could be official or personal communications intended for the staff member. If the RFID tag is associated with a patient, corresponding messages could include updates to the patient's medical records or prescribed medicine dosages.

The display device can have multiple embodiments. In a first embodiment, the display device is a hand-held RFID symbol reader. Hand-held RFID symbol readers are known in the art, and generally employ a small liquid crystal display (LCD) screen to show information stored on a RFID tag. Hand-held RFID symbol readers generally resemble a scanner gun or personal digital assistant (PDA). In a second embodiment, the display device is integrated directly with a RFID tag, in a manner similar to an ordinary alpha-numeric pager, having a LCD display coupled to the RFID tag, operable to display alpha-numeric text stored in the RFID tag's memory. The RFID tag with integrated display device can be used in place of an ordinary alpha-numeric pager for sending messages to people. A simplified version of the integrated display device has a indicator, such as a light emitting diode (LED), that turns on to indicate that a message has been received by the RFID tag, and that the message needs to be read using another display device. In the simplified integrated display, different colored LEDs can be used to indicate the importance of the message. For example, red may be used for a critical message, and green may be used for a message of normal importance. Similarly, a flashing LED can indicate a critical message, and a solid LED can indicate a message of normal importance. Other display devices could also be used, such as a RFID reader coupled directly to a general purpose computer or PDA that displays on a screen the information stored on a RFID tag.

One feature of the RFID Paging Infrastructure is that the apparatus is aware of the location of detected RFID tags. Because RFID transceivers only detect RFID tags within a localized vicinity, the location of the object to which the RFID tag is affixed is known based on which RFID transceiver detects the affixed RFID tag. With location awareness, the message intended for a RFID tag can change with the RFID tag's location. For example, a RFID tag on a piece of equipment assigned to one section of a hospital normally contains a message related to the piece of equipment's functional status. But if the piece of equipment is moved to another part of the hospital, the message can be changed to indicate that the piece of equipment is in the wrong place and needs to be returned. As another example, the location awareness of the RFID Paging Infrastructure enables personal messages to a surgeon to be blocked while the surgeon is in an operating room.

An additional embodiment of the RFID Paging Infrastructure routes messages intended for a first RFID tag to a second RFID tag when the first RFID tag can not be located. Thus, important messages can be sent to a RFID tag that an intended recipient is likely to scan with a hand-held display device, or to a RFID tag at a nearby location that has a LED indicator that the intended recipient is likely to see.

BRIEF DESCRIPTION OF DRAWINGS

The novel features believed characteristic of the invention are set forth in the appended claims. The invention itself, however, as well as a preferred mode of use, further objectives and advantages thereof, will be understood best by reference to the following detailed description of an illustrative embodiment when read in conjunction with the accompanying drawings, wherein:

DETAILED DESCRIPTION OF THE PREFERRED EMBODIMENT

The principles of the present invention are applicable to a variety of computer hardware and software configurations. The term "computer hardware" or "hardware," as used herein, refers to any machine or apparatus that is capable of accepting, performing logic operations on, storing, or displaying data, and includes without limitation processors and memory; the term "computer software" or "software," refers to any set of instructions operable to cause computer hardware to perform an operation. A "computer," as that term is used herein, includes without limitation any useful combination of hardware and software, and a "computer program" or "program" includes without limitation any software operable to cause computer hardware to accept, perform logic operations on, store, or display data. A computer program may, and often is, comprised of a plurality of smaller programming units, including without limitation subroutines, modules, functions, methods, and procedures. Thus, the functions of the present invention may be distributed among a plurality of computers and computer programs. The invention is described best, though, as a single computer program that configures and enables one or more general-purpose computers to implement the novel aspects of the invention. For illustrative purposes, the inventive computer program will be referred to as the "RFID Paging Infrastructure."

Figure 1:
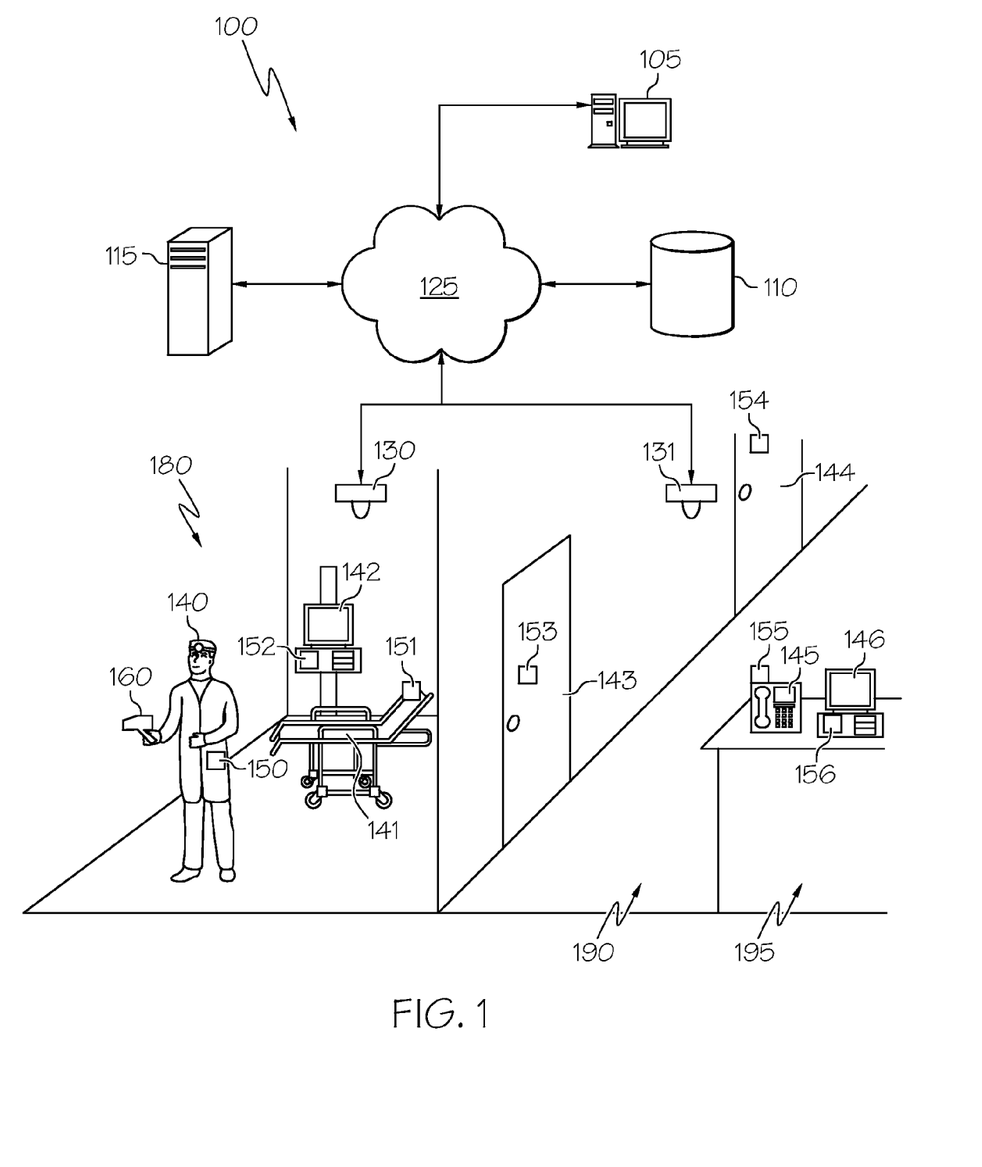
FIG. 1 is an exemplary computer network and RFID infrastructure.

Additionally, the RFID Paging Infrastructure is described below with reference to an exemplary network of hardware devices, as depicted in FIG. 1. A "network" comprises any number of hardware devices coupled to and in communication with each other through a communication medium, such as the Internet. A "communications medium" includes without limitation any physical, optical, electromagnetic, or other medium through which hardware or software can transmit data. For descriptive purposes, exemplary network 100 has only a limited number of nodes, including workstation computer 105, persistent storage 110, server computer 115, first RFID transceiver 130, and second RFID transceiver 131. Network connection 125 comprises all hardware, software, and communications media necessary to enable communication between network nodes 105-131. Unless otherwise indicated in context below, all network nodes use publicly available protocols or messaging services to communicate with each other through network connection 125.

FIG. 1 also shows the RFID Paging Infrastructure with reference to hospital room 180 and nurse station 195 located in hallway 190. First RFID transceiver 130 is located in hospital room 180, and second RFID transceiver 131 in located in hallway 190. Physician 140 is carrying first RFID tag 150 and RFID reader 160. Hospital room 180 has second RFID tag 151 affixed to bed 141, third RFID tag 152 affixed to medical monitor 142. Fourth RFID tag 153 is affixed to first door 143 in hallway 190. Fifth RFID tag 154 is affixed to second door 144 in Hallway 190. Nurse station 195 has telephone 145 with sixth RFID tag 155 and computer terminal 146 with seventh RFID tag 156. RFID tags 150-156 are active and programmable RFID tags.

Figure 2:
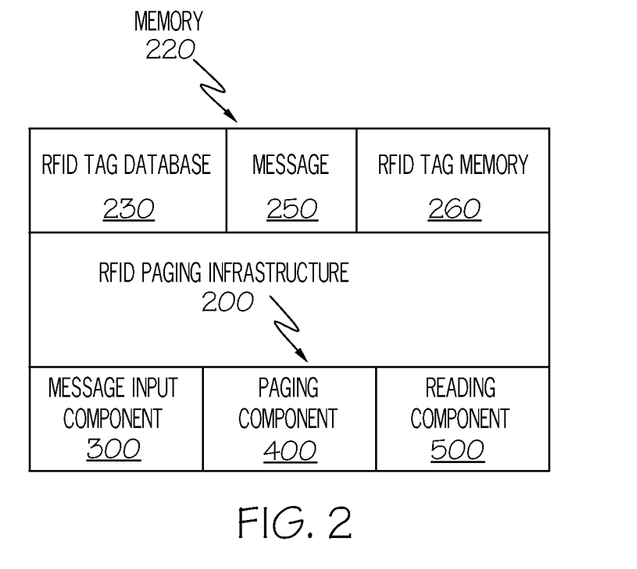
FIG. 2 describes programs and files in a memory on a computer.

RFID Paging Infrastructure 200 typically is stored in a memory, represented schematically as memory 220 in FIG. 2. The term "memory," as used herein, includes without limitation any volatile or persistent medium, such as an electrical circuit, magnetic disk, or optical disk, in which a computer can store data or software for any duration. A single memory may encompass and be distributed across a plurality of media. Further RFID Paging Infrastructure 200 may reside in more than one memory distributed across different computers, servers, logical partitions, or other hardware devices. The elements depicted in memory 220 may be located in, or distributed across, separate memories in any combination, and RFID Paging Infrastructure 200 may be adapted to identify, locate, and access any of the elements and coordinate actions, if any, by the distributed elements. Thus, FIG. 2 is included merely as a descriptive expedient and does not necessarily reflect any particular physical embodiment of memory 220. As depicted in FIG. 2, though, memory 220 may include additional data and programs. Of particular import to RFID Paging Infrastructure 200, memory 220 may include message 250 stored in RFID tag database 230, with which RFID Paging Infrastructure 200 interacts. RFID tag memory 260 is a rewritable persistent memory located on a RFID tag. RFID Paging Infrastructure 200 has three components: message input component 300, paging component 400, and reading component 500. Message input component 300 and Paging component 400 reside on a computer in direct communication with a RFID transceiver. Reading component 400 resides on a display device such as a hand-held RFID reader or an integrated RFID tag with a display.

Message 250 is an alphanumeric text message created by a person or a computer program. In the process of creating message 250, an intended RFID tag must be specified, using the intended RFID tag's identifier. Message 250, or a pointer indicating the location of message 250, is added to RFID tag database 230. RFID tag database 230 catalogs every known RFID tag identifier in use by the hospital, and all messages associated with each RFID tag, including message 250. Additionally, RFID tag database can be adapted to use an alias corresponding to a RFID tag identifier. For example, a room number, object description or asset ID number can be used as an alias for corresponding RFID tag identifiers. Likewise, a RFID tag carried by a physician can have a the physician's name or a phone number as an alias to identify the intended recipient of message 250. Message 250 can be created by directly typing text into a computer on network 100, or can be created by other methods of creating text messages known in the art. For example, message 250 can be created on a cell phone, a PDA, by an operator at an answering service or with a voice recognition software transcription of a telephonic voice message.

Figure 3:
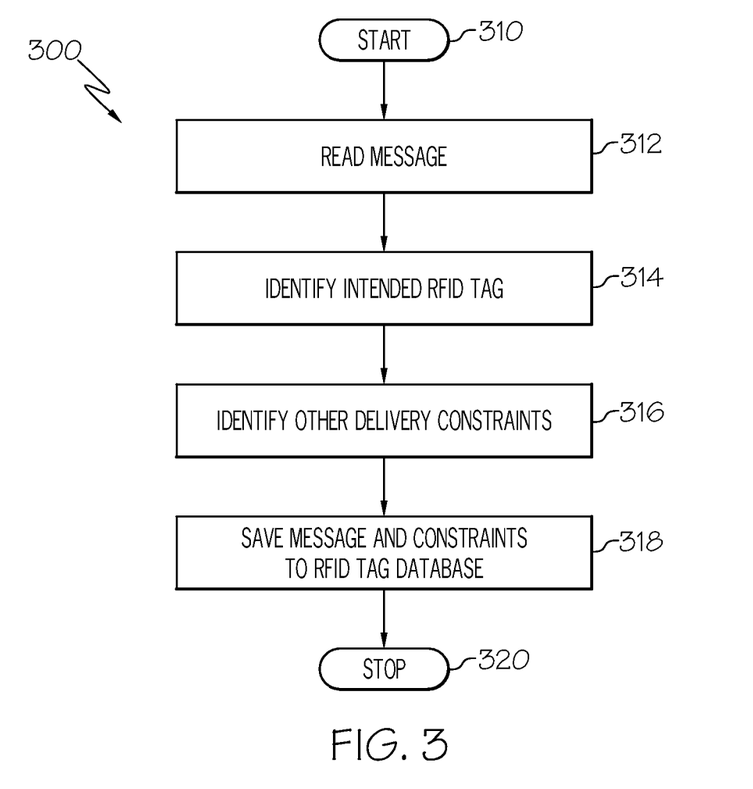
FIG. 3 is a flowchart of a message input component.

A flowchart of message input component 300 is shown by FIG. 3. Message input component 300 starts whenever alphanumeric text message 250 is received by message input component 300 (310). Message input component 300 reads message 250 (312) and identifies the intended RFID tag to receive message 250 (314). Message input component 300 identifies any other constraints placed on message 250 (316), such as a restriction placed on a delivery location or a restriction based on a message priority. Message input component 300 saves message 250 with constraints, if any, to a table with the intended RFID tag identifier in RFID tag database 230 (318) and stops (320).

Figure 4:
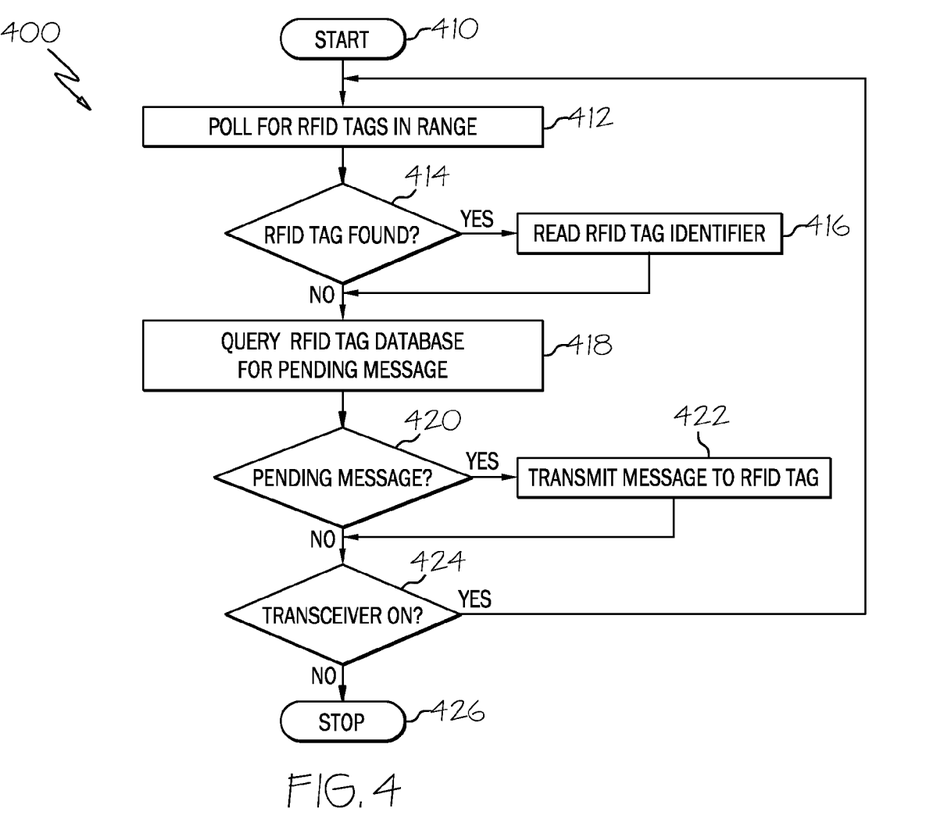
FIG. 4 is a flowchart of a paging component.

FIG. 4 shows paging component 400 start whenever a RFID transceiver is on (410). Paging component 400 causes the RFID transceiver to poll for RFID tags in range of the transceiver (412). If the transceiver finds a RFID tag (414), the transceiver reads the RFID tag's identifier (416). If no RFID tag is found, or after reading the RFID tag identifier at step 416, Paging component 400 queries RFID tag database 230 to determine if messages 250 is pending for the identified RFID tag (418). If message 250 is pending for the identified tag (420) paging component 400 causes the RFID transceiver to transmit message 250 to the identified RFID tag (422). For as long as the RFID transceiver is on (424), paging component 400 repeats steps 412 -424. Whenever the RFID transceiver is off, paging component 400 stops (426).

Figure 5:
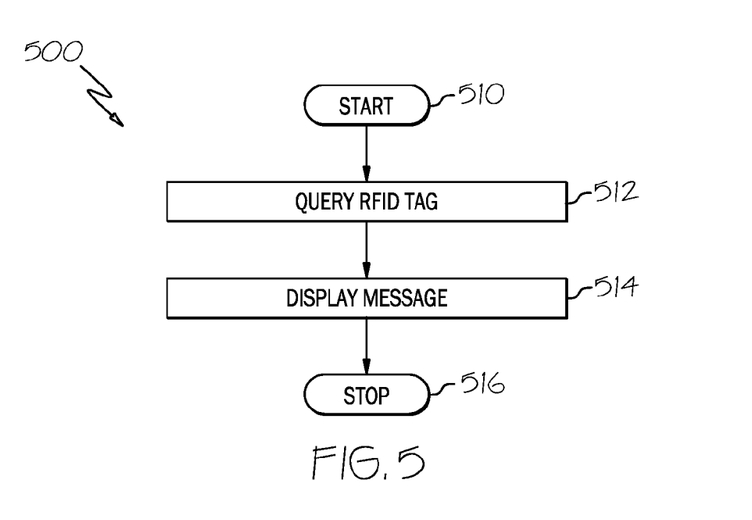
FIG. 5 is a flowchart of a reading component.
Figure 8:
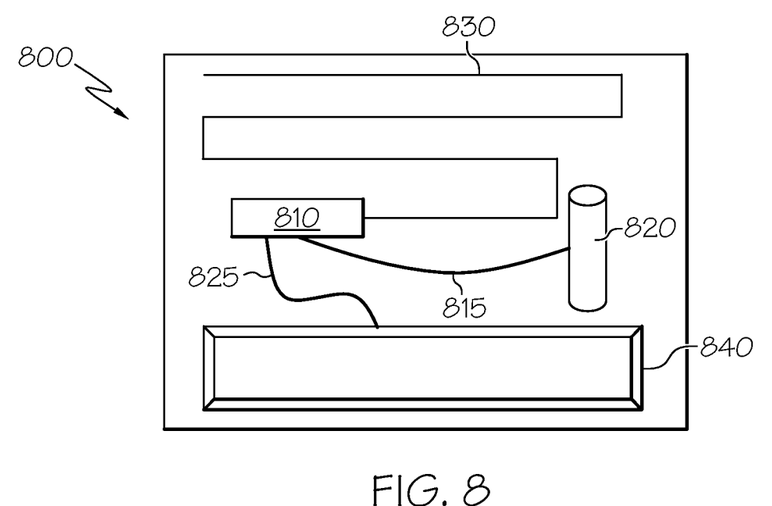
FIG. 8 shows the functional components of a RFID tag with an integrated display device.

A flowchart of reading component 500 is shown in FIG. 5. Reading component 500 starts whenever manually or automatically activated in the presence of a RFID tag (510). Reading component 500 queries the RFID tag (512) and displays the contents of any alpha-numeric text message, such as message 250 (514) then stops (516). For a RFID tag with an integrated display device, as shown in FIG. 8, reading component 500 will start automatically in response to message 250 being received by the RFID tag. For a hand-held RFID reader a display device (see FIG. 9), reading component 500 starts in response to a user pulling a trigger or otherwise activating the display device in the presence of a RFID tag containing message 250.

Because each RFID transceiver can only communicate with RFID tags in each RFID transceiver's local proximity, RFID paging infrastructure 200 has location awareness for each RFID tag. Location awareness allows RFID paging infrastructure 200 to intelligently change the contents and delivery method of message 250 based on the intended RFID tag's location. In one embodiment of RFID Paging Infrastructure 200 can change delivery of message 250 based on the priority of message 250 and the intended RFID tag's location. For example, if message 250 can't be sent to the intended RFID tag, message 250 is sent to related RFID tags. If an attempt to send an emergency page to Dr. Smith fails, the message can be sent to RFID tags on other devices or doctors near to Dr. Smith. In another example, both the contents and delivery location of message 250 change depending on the intended RFID tag's location. If Dr. Smith's patient needs immediate assistance, but Dr. Smith is in another wing of the hospital, RFID paging infrastructure 200 can page Dr. Jones who is just down the hall from the patient in addition to paging Dr. Smith. Message 250 can notify Dr. Jones to go to the patient immediately, while notifying Dr. Smith that Dr. Jones needs his help. In another example, the contents of message 250 change depending on the intended RFID tag's location in relation to other RFID tags. If RFID paging infrastructure 200 is aware that the medical equipment Dr. Smith needs for a patent is located in the treatment room next door, message 250 can provide information to Dr. Smith regarding the location of the equipment needed to treat the patent.

Figure 6:
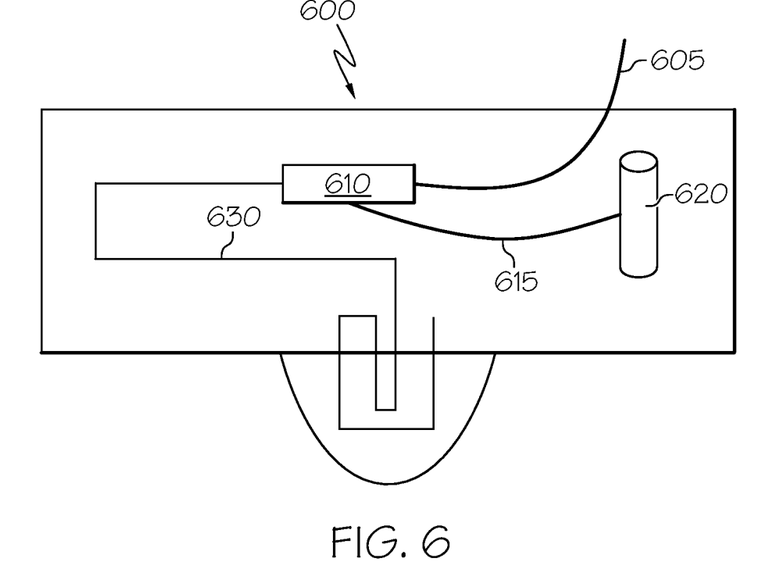
FIG. 6 shows the functional components of a RFID transceiver.

FIG. 6 shows the functional components of RFID transceiver 600. Logic component 610 is an integrated circuit performing and controlling the communication functions of transceiver 600. First connection 605 connects logic component 610 with a computer to facilitate communication with message input component 300 and paging component 400 of RFID Paging Infrastructure 200. Second connection 615 connects logic component 610 to power source 620 which can be a local power source, such as a rechargeable battery, or an external power source, such as a standard 110 volt electrical outlet. Antenna 630 enables logic component 610 to communicate with RFID tags in the vicinity of RFID transceiver 600.

Figure 7:
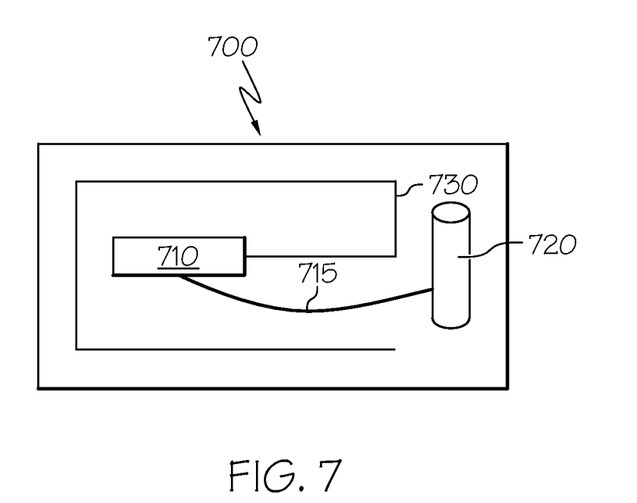
FIG. 7 shows the functional components of a RFID tag.

FIG. 7 shows the functional components of RFID tag 700. Logic component 710 is an integrated circuit performing and controlling the communication functions of RFID tag 700 and includes a portion of persistent memory for storing message 250. First connection 715 connects logic component 710 to power source 720 which can be a local power source, such as a replaceable or rechargeable battery, or an external power source, such as a powered port on a computer, or a powered port on some other type of hardware to which RFID tag 700 may be affixed. In another embodiment of RFID tag 700, power source 720 is a large antenna that receives power induced by radio waves from RFID transceiver 600. Antenna 730 enables logic component 710 to communicate with RFID transceiver 600 and with an external display device, such as hand-held RFID reader 900 (shown in FIG. 9).

FIG. 8 shows the functional components of RFID tag 800 with an integrated display device. Logic component 810 is an integrated circuit performing and controlling the communication functions of RFID tag 800 and includes a portion of persistent memory for storing message 250. Logic component 810 is capable of performing the functions of reading component 500 and controlling display panel 840. First connection 815 connects logic component 810 to power source 820 which can be a local power source, such as a replaceable or rechargeable battery, or an external power source, as described above. Antenna 830 enables logic component 810 to communicate with RFID transceiver 600. Second connection 825 connects logic component 810 to display panel 840. Display panel 840 can be a LCD that displays message 250, or display panel 840 can be any other known method of display alpha-numeric text. In a simplified embodiment of RFID tag 800, display panel 840 comprises an indicator that message 250 has been received and stored by RFID tag 800. In the simplified embodiment, display panel 840 may be one or more solid or blinking LEDs of one or more colors that can indicate priority of received message 250. An external display device is required to actually read the contents of message 250 when using the simplified embodiment of RFID tag 800.

Figure 9:
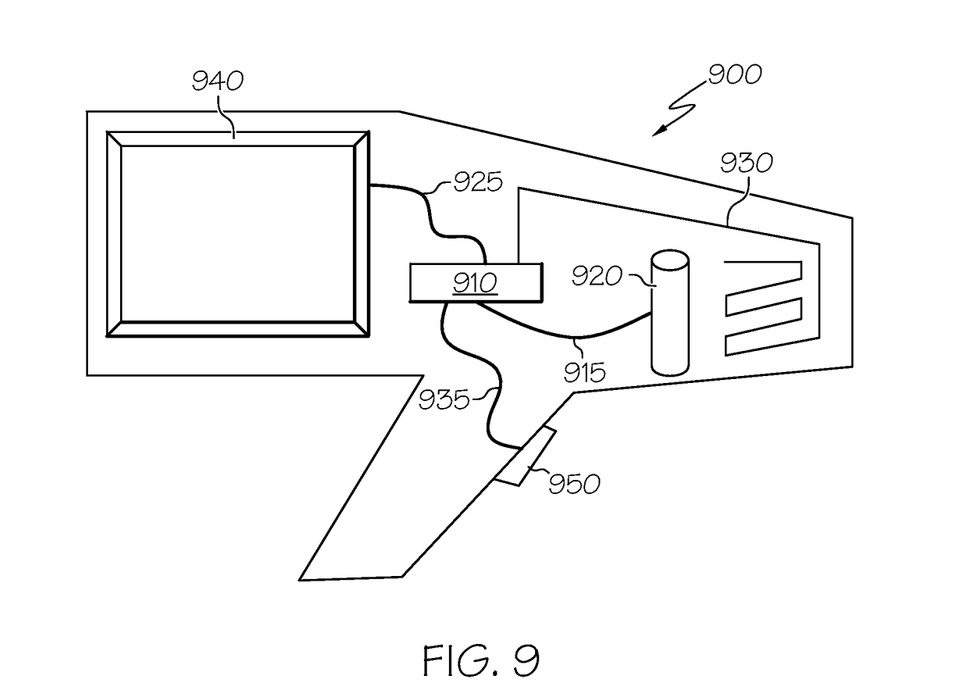
FIG. 9 shows the functional components of a hand-held RFID reader embodiment of a display device.

FIG. 9 shows the functional components of display device 900. Display device 900 is shown here as a hand-held RFID reader, which is known in the art. Logic component 910 is an integrated circuit performing and controlling the communication functions of display device 900 and is capable of performing the functions of reading component 500 to control display panel 940. First connection 915 connects logic component 910 to power source 920 which can be a local power source, such as a replaceable or rechargeable battery, or an external power source, as described above. Antenna 930 enables logic component 910 to communicate with RFID tag 700. Second connection 925 connects logic component 910 to display panel 940. Display panel 940 can be a LCD that displays message 250, or display panel 940 can be any other known method of displaying alpha-numeric text. Third connection 935 connects logic component 910 to trigger 950. Trigger 950 is used to activate display device 900 and start reading component 500.

A preferred form of the invention has been shown in the drawings and described above, but variations in the preferred form will be apparent to those skilled in the art. The preceding description is for illustration purposes only, and the invention should not be construed as limited to the specific form shown and described. The scope of the invention should be limited only by the language of the following claims.

What is claimed is:

1. A computer implemented process for transmitting a text message for storage on a RFID tag, the computer implemented process comprising:
   providing a plurality of RFID transceivers, a RFID tag database, and a plurality of RFID tags, each RFID tag having a transmitter, a memory, and a receiver, wherein the RFID tag database catalogs all known RFID tag identifiers and all text messages associated with each of the plurality of RFID tags and wherein each of the plurality of RFID tags are attached to a person or an object;
   continuously polling, by each RFID transceiver, for RFID tags in range, and responsive to finding a particular RFID tag that is in a range of a particular RFID transceiver at a particular location, determining a location of the one of the person and the object to which the particular RFID tag is attached as the particular location, reading the particular RFID tag's identifier, querying the RFID tag database to determine whether a corresponding text message is pending for the particular RFID tag's identifier, and when a corresponding text message is pending for the particular RFID tag's identifier, sending the corresponding text message to the particular RFID tag having the particular RFID tag's identifier; and
   responsive to the location of the one of the person and the object having changed from a first location associated with a first RFID transceiver to the particular location associated with the particular RFID transceiver, changing a content of the corresponding text message to a different message configured for the second location.

2. The computer implemented process of claim 1 wherein the display device is a hand-held RFID tag reader and further comprises a light emitting diode that indicates that the text message has been received and stored by the RFID tag.

3. The computer implemented process of claim 1 wherein the display device is coupled directly with the RFID tag.

4. The computer implemented process of claim 1 wherein the RFID tag is affixed to a particular piece of equipment, wherein one or more text messages are assigned and routed to the RFID tag regarding an assigned location of the particular piece of equipment.

5. The computer implemented process of claim 4 wherein the text message intended for the RFID tag relates to the status of the particular piece of equipment and a maintenance schedule of the particular piece of equipment.

6. The computer implemented process of claim 1 wherein the text message is sent to a plurality of RFID tags, each of the plurality of RFID tags associated with an alias, the alias being a name of a location, an object description, an asset identification number, a person's name or a phone number.

7. The computer implemented process of claim 1 wherein the text message intended for the RFID tag is one of a personal and an official communication for-the person carrying the RFID tag, and wherein a constraint associated with the particular location is included with the text message and prevents delivery to the RFID tag when the RFID tag is in the particular location, and wherein the text message is created by a voice recognition software transcription of a telephonic voice message.

8. An apparatus for transmitting a message, the apparatus comprising:
   a plurality of RFID transceivers connected to a network;
   a plurality of RFID tags, each RFID tag having a storage and display, each RFID tag connected to the network;
   a processor connected to the network;
   a memory connected to the processor;
   a database in the memory, connected to the network, comprising a table with a listing of a plurality of RFID tag identifiers, each RFID tag identifier corresponding to a particular RFID tag and a particular message intended for the particular RFID tag, wherein the database catalogs all known RFID tag identifiers and all text messages associated with each of the plurality of RFID tags, and wherein each particular RFID tag is associated with an intended recipient of each particular text message and wherein each of the plurality of RFID tags are attached to a person or an object;
   a paging program in the memory operable to detect one or more of the RFID tags, read an identifier from a detected RFID tag, determine that a text message is intended for the detected RFID tag, responsive to a determination that the text message is intended for the detected RFID tag, transmit the text message to the detected RFID tag, and save the text message in a RFID tag memory on the detected RFID tag;
   a display device operable to display the message stored in the RFID memory on the detected RFID tag; and
   wherein each RFID transceiver continuously polls for RFID tags in range, and responsive to finding a particular RFID tag that is in a range of a particular RFID transceiver, determines a location of the one of the person and the object to which the particular RFID tag is attached, reading the particular RFID tag's identifier, queries the database to determine whether a corresponding text message is pending for the particular RFID tag's identifier, and when a corresponding text message is pending for the particular RFID tag's identifier, sending the corresponding text message to the particular RFID tag having the particular RFID tag's identifier; and
   wherein, responsive to the location of the one of the person and the object having changed from a first location associated with a first RFID transceiver to a second location associated with the particular RFID transceiver, changing a content of the corresponding text message to a different message configured for the second location.

9. The apparatus of claim 8 wherein the display device is a hand-held RFID tag reader and further comprises a light emitting diode that indicates that the text message has been received and stored by the by the RFID tag.

10. The apparatus of claim 8 wherein the display device is coupled directly with the RFID tag.

11. The apparatus of claim 8 wherein the RFID tag is affixed to a particular piece of equipment, wherein one or more text messages are assigned and routed to the RFID tag regarding an assigned location of the particular piece of equipment.

12. The apparatus of claim 11 wherein the text message intended for the RFID tag relates to the status of the particular piece of equipment and a maintenance schedule of the particular piece of equipment.

13. The apparatus of claim 8 wherein the message is sent to an RFID tag based on an alias associated with the RFID tag, the alias being a name of a location, an object description, an asset identification number, a person's name or a phone number.

14. The apparatus of claim 8 wherein the text message intended for the RFID tag is one of a personal and an official communication for the person carrying the RFID tag and wherein a constraint associated with the particular location and with the text message prevents delivery to the RFID tag when the RFID tag is in the particular location, and wherein the text message is created by a voice recognition software transcription of a telephonic voice message.

15. The apparatus of claim 8 wherein the paging program is further operable to determine the location of the RFID tag and transmit the text message based on the location of the RFID tag.

16. The apparatus of claim 8 wherein the RFID tag is carried by a medical patient.

17. The apparatus of claim 16 wherein the text message intended for the RFID tag contains medical records for the medical patient carrying the RFID tag.

18. The apparatus of claim 8 wherein the RFID tag is affixed to one or more of the following at a medical facility: a room, a bed, a hallway, a medical monitor a door, a nurse station telephone, and a computer terminal at a medical facility.

19. The apparatus of claim 18 wherein the text message intended for the RFID tag contains information related to the contents and occupants of the room.

20. The apparatus of claim 8 wherein the paging program is further operable to identify a critically important text message in the database intended for a first RFID tag, search for the intended first RFID tag and responsive to not locating the first RFID tag, transmitting the text message to a second RFID tag.

21. The computer implemented method of claim 1 further comprising:
   connecting the plurality of RFID transceivers and the RFID tag database to a network;
   creating a plurality of text messages by a processor of a computer connected to the network;
   including one or more constraints in one or more of the plurality of text messages;
   storing the plurality of text messages in the RFID tag database, each of the plurality of text messages associated with an identifier, wherein the identifier is associated with an intended recipient of a particular text message;
   using the plurality of RFID transceivers, detecting, by the processor, a RFID tag of the plurality of RFID tags and determining, by the processor, a location of the RFID tag;
   reading, by the processor, an identifier from the RFID tag;
   determining, by the processor, whether the text message is intended for the RFID tag by comparing the RFID's tag's identifier with one or more stored identifiers associated with text messages in the RFID tag database;
   responsive to a determination that a particular text message is associated in the RFID tag database with a stored identifier that is the same as the RFID tag's identifier, transmitting the text message associated with the stored identifier to the RFID tag;
   storing the text message in a memory on the RFID tag; and
   displaying the text message on the RFID tag on an alpha-numeric display device.

22. The computer implemented method of claim 1 further comprising:
   changing a delivery method of the corresponding text message to a different delivery method configured for the second location.

23. The apparatus of claim 8 further comprising:
   wherein the plurality of RFID transceivers and the RFID tag database are connected to a network;
   wherein a plurality of text messages are created by a processor of a computer connected to the network;
   wherein one or more constraints are included in one or more of the plurality of text messages;
   wherein the plurality of text messages are stored in the RFID tag database, each of the plurality of text messages associated with an identifier, wherein the identifier is associated with an intended recipient of a particular text message;
   wherein using the plurality of RFID transceivers, a RFID tag of the plurality of RFID tags is detected;
   wherein a location of the RFID tag is determined;
   wherein an identifier is read from the RFID tag;
   wherein whether the text message is intended for the RFID tag is determined by comparing the RFID's tag's identifier with one or more stored identifiers associated with text messages in the RFID tag database;
   wherein responsive to a determination that a particular text message is associated in the RFID tag database with a stored identifier that is the same as the RFID tag's identifier, the text message associated with the stored identifier to the RFID tag is transmitted;
   wherein the text message is stored in a memory on the RFID tag; and
   wherein the text message on the RFID tag is displayed on an alpha-numeric display device.

24. The apparatus of claim 8 further comprising:
   wherein a delivery method of the corresponding text message is changed to a different delivery method configured for the second location.

* * * * *